US009220826B2

(12) United States Patent
D'Ambrosio

(10) Patent No.: US 9,220,826 B2
(45) Date of Patent: Dec. 29, 2015

(54) METHOD AND APPARATUS FOR ACCURATELY TRACKING AVAILABLE CHARGE IN A TRANSCUTANEOUS ENERGY TRANSFER SYSTEM

(75) Inventor: Ralph L. D'Ambrosio, Wenham, MA (US)

(73) Assignee: Abiomed, Inc., Danvers, MA (US)

( * ) Notice: Subject to any disclaimer, the term of this patent is extended or adjusted under 35 U.S.C. 154(b) by 0 days.

(21) Appl. No.: 13/328,610

(22) Filed: Dec. 16, 2011

(65) Prior Publication Data

US 2012/0157755 A1    Jun. 21, 2012

Related U.S. Application Data

(60) Provisional application No. 61/425,162, filed on Dec. 20, 2010.

(51) Int. Cl.
*A61N 1/08* (2006.01)
*A61M 1/12* (2006.01)
*A61M 1/10* (2006.01)
*H02J 7/00* (2006.01)

(52) U.S. Cl.
CPC ............ *A61M 1/127* (2013.01); *A61M 1/1086* (2013.01); *A61M 1/122* (2014.02); *A61M 2205/17* (2013.01); *A61M 2205/18* (2013.01); *A61M 2205/3523* (2013.01); *A61M 2205/50* (2013.01); *A61M 2205/8206* (2013.01); *A61M 2205/8243* (2013.01); *H02J 2007/005* (2013.01)

(58) Field of Classification Search
CPC ... A61N 1/3708; A61N 1/378; A61N 1/3787; A61M 1/127; A61M 1/1086; A61M 1/122; A61M 2205/17

USPC .................... 600/16; 607/8, 27, 29
See application file for complete search history.

(56) References Cited

U.S. PATENT DOCUMENTS

| 3,195,038 A | 7/1965 | Fry |
| 3,195,540 A | 7/1965 | Waller |
| 3,357,432 A | 12/1967 | Sparks |
| 3,357,434 A | 12/1967 | Abell |
| 3,711,747 A | 1/1973 | Sahara et al. |

(Continued)

FOREIGN PATENT DOCUMENTS

| DE | 2720011 A1 | 11/1978 |
| EP | 0 507 360 A2 | 10/1992 |

(Continued)

OTHER PUBLICATIONS

[No Author Listed] SBS 1.1-Compliant Gas Gauge and Protection Enabled with Impedance Track™, Texas Instruments, SLUS757B—Jul. 2007, Revised Apr. 2008. 18 pages.

(Continued)

*Primary Examiner* — Christopher D Koharski
*Assistant Examiner* — Michael Carey
(74) *Attorney, Agent, or Firm* — Ropes & Gray LLP

(57) ABSTRACT

Improved devices and methods for tracking power consumption and available charge in a transcutaneous energy transfer (TET) system are provided. The method includes measuring the available charge in a battery and the current rate of power consumption in an implanted medical device, determining the remaining time before the charge level of the battery reaches a predetermined threshold level, and communicating the remaining time to a user.

13 Claims, 7 Drawing Sheets

(56) References Cited

U.S. PATENT DOCUMENTS

| | | |
|---|---|---|
| 3,756,246 A | 9/1973 | Thaler et al. |
| 3,824,129 A | 7/1974 | Fagan, Jr. |
| 3,825,925 A | 7/1974 | Drusch |
| 3,866,616 A | 2/1975 | Purdy et al. |
| 3,867,950 A | 2/1975 | Fischell |
| 3,888,260 A | 6/1975 | Fischell |
| 3,915,038 A | 10/1975 | Malin |
| 3,934,177 A | 1/1976 | Horbach |
| 3,942,535 A | 3/1976 | Schulman |
| 3,987,799 A | 10/1976 | Purdy et al. |
| 3,995,137 A | 11/1976 | Okada et al. |
| 4,011,499 A | 3/1977 | Betsill et al. |
| 4,012,769 A | 3/1977 | Edwards et al. |
| 4,041,955 A | 8/1977 | Kelly et al. |
| 4,068,292 A | 1/1978 | Berry et al. |
| 4,071,032 A | 1/1978 | Schulman |
| 4,104,701 A | 8/1978 | Baranowski |
| 4,134,408 A | 1/1979 | Brownlee et al. |
| 4,143,661 A | 3/1979 | LaForge et al. |
| 4,186,749 A | 2/1980 | Fryer |
| 4,266,533 A | 5/1981 | Ryaby et al. |
| 4,441,210 A | 4/1984 | Hochmair et al. |
| 4,441,498 A | 4/1984 | Nordling |
| 4,517,585 A | 5/1985 | Ridout et al. |
| 4,539,433 A | 9/1985 | Ishino et al. |
| 4,586,508 A | 5/1986 | Batina et al. |
| 4,665,896 A | 5/1987 | LaForge et al. |
| 4,673,888 A | 6/1987 | Engelmann et al. |
| 4,678,986 A | 7/1987 | Barthelemy |
| 4,679,560 A | 7/1987 | Galbraith |
| 4,716,353 A | 12/1987 | Engelmann |
| 4,717,889 A | 1/1988 | Engelmann |
| 4,741,339 A | 5/1988 | Harrison et al. |
| 4,808,924 A | 2/1989 | Cecco et al. |
| 4,837,497 A | 6/1989 | Leibovich |
| 4,924,171 A | 5/1990 | Baba et al. |
| 4,925,443 A | 5/1990 | Heilman et al. |
| 4,944,299 A | 7/1990 | Silvian |
| 5,000,178 A | 3/1991 | Griffith |
| 5,004,489 A | 4/1991 | Rotman |
| 5,109,843 A | 5/1992 | Melvin et al. |
| 5,214,392 A | 5/1993 | Kobayashi et al. |
| 5,312,439 A | 5/1994 | Loeb |
| 5,314,453 A | 5/1994 | Jeutter |
| 5,324,316 A | 6/1994 | Schulman et al. |
| 5,350,411 A | 9/1994 | Ryan et al. |
| 5,350,413 A | 9/1994 | Miller et al. |
| 5,355,296 A | 10/1994 | Kuo et al. |
| 5,358,514 A | 10/1994 | Schulman et al. |
| 5,383,912 A | 1/1995 | Cox et al. |
| 5,411,536 A | 5/1995 | Armstrong |
| 5,411,537 A | 5/1995 | Munshi et al. |
| 5,480,415 A | 1/1996 | Cox et al. |
| 5,506,503 A | 4/1996 | Cecco et al. |
| 5,527,348 A | 6/1996 | Winkler et al. |
| 5,545,191 A | 8/1996 | Mann et al. |
| 5,556,421 A | 9/1996 | Prutchi et al. |
| 5,569,156 A | 10/1996 | Mussivand |
| 5,613,935 A | 3/1997 | Jarvik |
| 5,621,369 A | 4/1997 | Gardner et al. |
| 5,630,836 A | 5/1997 | Prem et al. |
| 5,690,693 A | 11/1997 | Wang et al. |
| 5,702,431 A | 12/1997 | Wang et al. |
| 5,713,939 A | 2/1998 | Nedungadi et al. |
| 5,722,998 A | 3/1998 | Prutchi et al. |
| 5,730,125 A | 3/1998 | Prutchi et al. |
| 5,733,313 A | 3/1998 | Barreras, Sr. et al. |
| 5,735,887 A | 4/1998 | Barreras, Sr. et al. |
| 5,740,257 A | 4/1998 | Marcus |
| 5,741,316 A | 4/1998 | Chen et al. |
| 5,749,909 A | 5/1998 | Schroeppel et al. |
| 5,755,748 A | 5/1998 | Borza et al. |
| 5,861,019 A | 1/1999 | Sun |
| 5,948,006 A | 9/1999 | Mann |
| 5,951,459 A | 9/1999 | Blackwell |
| 5,959,522 A | 9/1999 | Andrews |
| 5,963,132 A | 10/1999 | Yoakum |
| 5,978,713 A | 11/1999 | Prutchi et al. |
| 5,991,665 A * | 11/1999 | Wang et al. ............ 607/61 |
| 5,995,874 A | 11/1999 | Borza et al. |
| 6,047,214 A | 4/2000 | Mueller et al. |
| 6,048,601 A | 4/2000 | Yahagi et al. |
| 6,058,330 A | 5/2000 | Borza et al. |
| 6,067,474 A | 5/2000 | Schulman et al. |
| 6,141,592 A | 10/2000 | Pauly |
| 6,144,841 A | 11/2000 | Feeney |
| 6,149,683 A | 11/2000 | Lancisi et al. |
| 6,212,430 B1 | 4/2001 | Kung |
| 6,243,608 B1 | 6/2001 | Pauly et al. |
| 6,275,737 B1 | 8/2001 | Mann |
| 6,278,258 B1 | 8/2001 | Echarri et al. |
| 6,321,118 B1 | 11/2001 | Hahn |
| 6,324,430 B1 | 11/2001 | Zarinetchi et al. |
| 6,324,431 B1 | 11/2001 | Zarinetchi et al. |
| 6,327,504 B1 | 12/2001 | Dolgin et al. |
| 6,349,234 B2 | 2/2002 | Pauly et al. |
| 6,366,817 B1 | 4/2002 | Kung |
| 6,389,318 B1 | 5/2002 | Zarinetchi et al. |
| 6,395,027 B1 | 5/2002 | Snyder |
| 6,400,991 B1 | 6/2002 | Kung |
| 6,415,186 B1 | 7/2002 | Chim et al. |
| 6,430,444 B1 | 8/2002 | Borza et al. |
| 6,442,434 B1 | 8/2002 | Zarinetchi et al. |
| 6,443,891 B1 | 9/2002 | Grevious |
| 6,445,956 B1 | 9/2002 | Laird et al. |
| 6,478,820 B1 | 11/2002 | Weiss |
| 6,496,733 B2 | 12/2002 | Zarinetchi et al. |
| 6,507,759 B1 | 1/2003 | Prutchi et al. |
| 6,542,777 B1 | 4/2003 | Griffith et al. |
| 6,553,263 B1 | 4/2003 | Meadows et al. |
| 6,591,139 B2 | 7/2003 | Loftin et al. |
| 6,631,296 B1 | 10/2003 | Parramon et al. |
| 6,745,077 B1 | 6/2004 | Griffith et al. |
| 6,748,273 B1 * | 6/2004 | Obel et al. ............ 607/29 |
| 6,772,011 B2 | 8/2004 | Dolgin |
| 6,959,213 B2 | 10/2005 | Prutchi et al. |
| 6,959,217 B2 | 10/2005 | DelMain et al. |
| 6,968,234 B2 | 11/2005 | Stokes |
| 7,015,769 B2 | 3/2006 | Schulman et al. |
| 7,027,871 B2 | 4/2006 | Burnes et al. |
| 7,062,331 B2 | 6/2006 | Zarinetchi et al. |
| 7,076,304 B2 | 7/2006 | Thompson |
| 7,079,901 B1 | 7/2006 | Loftin et al. |
| 7,092,762 B1 | 8/2006 | Loftin et al. |
| 7,151,914 B2 | 12/2006 | Brewer |
| 7,155,291 B2 | 12/2006 | Zarinetchi et al. |
| 7,177,690 B2 | 2/2007 | Woods et al. |
| 7,184,836 B1 | 2/2007 | Meadows et al. |
| 7,191,007 B2 | 3/2007 | Desai et al. |
| 7,225,032 B2 | 5/2007 | Schmeling et al. |
| 7,237,712 B2 | 7/2007 | DeRocco et al. |
| 7,248,929 B2 | 7/2007 | Meadows et al. |
| 7,286,880 B2 | 10/2007 | Olson et al. |
| 7,286,881 B2 | 10/2007 | Schommer et al. |
| 7,295,878 B1 | 11/2007 | Meadows et al. |
| 7,308,316 B2 | 12/2007 | Schommer |
| 7,418,297 B2 | 8/2008 | Bornhoft et al. |
| 7,437,644 B2 | 10/2008 | Ginggen et al. |
| 7,471,986 B2 | 12/2008 | Hatlestad |
| 7,482,783 B2 | 1/2009 | Schommer |
| 7,512,443 B2 | 3/2009 | Phillips et al. |
| 7,515,012 B2 | 4/2009 | Schulman et al. |
| 7,515,967 B2 | 4/2009 | Phillips et al. |
| 7,532,932 B2 | 5/2009 | Denker et al. |
| 7,599,743 B2 | 10/2009 | Hassler, Jr. et al. |
| 7,599,744 B2 | 10/2009 | Giordano et al. |
| 7,632,235 B2 | 12/2009 | Karicherla |
| 7,658,196 B2 | 2/2010 | Ferreri et al. |
| 7,689,176 B2 | 3/2010 | Crivelli |
| 7,711,435 B2 | 5/2010 | Schommer |
| 7,738,965 B2 | 6/2010 | Phillips et al. |
| 7,751,899 B1 | 7/2010 | Karunasiri |
| 7,751,902 B1 | 7/2010 | Karunasiri |
| 7,775,444 B2 | 8/2010 | DeRocco et al. |

(56) References Cited

U.S. PATENT DOCUMENTS

| | | | |
|---|---|---|---|
| 7,813,801 B2 | 10/2010 | Youker et al. | |
| 7,818,068 B2 | 10/2010 | Meadows et al. | |
| 7,822,480 B2 | 10/2010 | Park et al. | |
| 7,848,814 B2 | 12/2010 | Torgerson et al. | |
| 7,856,986 B2 | 12/2010 | Darley | |
| 2002/0016568 A1 | 2/2002 | Lebel et al. | |
| 2003/0065366 A1* | 4/2003 | Merritt et al. | 607/27 |
| 2003/0088295 A1 | 5/2003 | Cox et al. | |
| 2003/0163020 A1 | 8/2003 | Frazier | |
| 2003/0171792 A1 | 9/2003 | Zarinetchi et al. | |
| 2004/0039423 A1 | 2/2004 | Dolgin | |
| 2005/0075693 A1 | 4/2005 | Toy et al. | |
| 2005/0075696 A1 | 4/2005 | Forsberg et al. | |
| 2005/0107847 A1 | 5/2005 | Gruber et al. | |
| 2005/0113887 A1 | 5/2005 | Bauhahn et al. | |
| 2005/0288739 A1 | 12/2005 | Hassler et al. | |
| 2005/0288740 A1 | 12/2005 | Hassler et al. | |
| 2005/0288743 A1 | 12/2005 | Ahn et al. | |
| 2006/0020300 A1 | 1/2006 | Nghieum et al. | |
| 2006/0020305 A1 | 1/2006 | Desai et al. | |
| 2006/0107148 A1 | 5/2006 | Ginggen et al. | |
| 2006/0197494 A1 | 9/2006 | Schommer | |
| 2006/0247737 A1 | 11/2006 | Olson et al. | |
| 2007/0049983 A1 | 3/2007 | Freeberg | |
| 2007/0106274 A1 | 5/2007 | Ayre et al. | |
| 2007/0142696 A1 | 6/2007 | Crosby et al. | |
| 2007/0255349 A1 | 11/2007 | Torgerson et al. | |
| 2007/0270921 A1 | 11/2007 | Strother et al. | |
| 2008/0027500 A1 | 1/2008 | Chen | |
| 2008/0027513 A1 | 1/2008 | Carbunaru | |
| 2008/0065290 A1 | 3/2008 | Breed | |
| 2008/0129517 A1 | 6/2008 | Crosby et al. | |
| 2008/0167531 A1 | 7/2008 | McDermott | |
| 2008/0312852 A1* | 12/2008 | Maack | 702/63 |
| 2009/0069869 A1 | 3/2009 | Stouffer et al. | |
| 2009/0157148 A1 | 6/2009 | Phillips et al. | |
| 2009/0273349 A1 | 11/2009 | Rondoni et al. | |
| 2009/0276016 A1 | 11/2009 | Phillips et al. | |
| 2010/0063347 A1 | 3/2010 | Yomtov | |
| 2010/0076524 A1 | 3/2010 | Forsberg et al. | |
| 2010/0080025 A1 | 4/2010 | Terlizzi | |
| 2010/0222848 A1 | 9/2010 | Forsell | |
| 2010/0305662 A1 | 12/2010 | Ozawa et al. | |
| 2010/0312188 A1 | 12/2010 | Robertson | |
| 2011/0009924 A1 | 1/2011 | Meskens | |
| 2011/0101790 A1 | 5/2011 | Budgett | |
| 2011/0160516 A1 | 6/2011 | Dague et al. | |
| 2011/0196452 A1 | 8/2011 | Forsell | |
| 2011/0278948 A1 | 11/2011 | Forsell | |
| 2012/0154143 A1 | 6/2012 | D'Ambrosio | |
| 2012/0157753 A1 | 6/2012 | D'Ambrosio | |
| 2012/0157754 A1 | 6/2012 | D'Ambrosio | |
| 2012/0265003 A1 | 10/2012 | D'Ambrosio | |
| 2013/0158631 A1 | 6/2013 | Shea et al. | |

FOREIGN PATENT DOCUMENTS

| | | |
|---|---|---|
| JP | 07-046164 A | 2/1995 |
| JP | 2010-284065 A | 12/2010 |
| WO | 97/29802 A2 | 8/1997 |
| WO | 97/47065 A1 | 12/1997 |
| WO | 99/44684 A1 | 9/1999 |
| WO | 2006096685 A1 | 9/2006 |
| WO | 2008/106717 A1 | 9/2008 |
| WO | 2011008163 A1 | 1/2011 |

OTHER PUBLICATIONS

[No Author Listed] Low-power SoC (system-on-chip) with MCU, memory sub-1 ghz RF transceiver, and USB controller. TIRF Common Spec (CC1110Fx/CC1111Fx), Texas Instruments, Jul. 20, 2010, 247 pages.

[No Author Listed]Battery Spec NCR 18650. NNP Series. Panasonic. Feb. 2010, 1 page.

Abe et al., Development of transcutaneous energy transmission system for totally implantable artificial heart. Artificial Heart 2/Proceedings of the 2nd International Symposium on Artificial Heart and Assist Device. Akutsu, T. ed, Springer-Verlag, Tokyo, pp. 257-261, 1988.

Ahn et al., In Vivo Performance Evaluation of a Transcutaneous Energy and Information Transmission System for the Total Artificial Heart, ASAIO Journal 1993, M208-M212.

Barsukov, Theory and Implementation of Impedance Track™ Battery Fuel-Gauging Algorithm in bq20z8x Product Family, Texas Instruments, SLUA364, Nov. 2005. 8 pages.

Bearnson et al., Electronics Development for the Utah Electrohydrolic Total Artificial Heart. Sixth Annual IEEE Symposium on Computer-Based Medical Systems, 247-252 (1993).

Callewaert et al., A Programmable Implantable Stimulator with Percutaneous Optical Control. Ninth Annual Conference of the Engineering in Medicine and Biology Society IEEE, 1370-1371 (1987).

Davies et al., Adaptation of Tissue to a Chronic Heat Load, ASAIO Journal. 40(3), M514-7 (1994).

Donaldson, Nde N, Use of feedback with voltage regulators for implants powered by coupled coils. Med Biol Eng Comput. May 1985;23(3):291, XP002066875, ISSN: 0140-0118.

Fraim et al. Performance of a tuned ferrite core transcutaneous transformer. IEEE Trans Bio-med Eng. Sep. 1971;BME-18(5):352-9.

Galbraith et al, A Wide-Band Efficient Inductive Transdermal Power and Data Link with Coupling Insensitive Gain. IEEE Transactions on Biomedical Engineering, BME 34(4):265-275 (1987).

Geselowitz et al., The effects of metals on a transcutaneous energy transmission system. IEEE Transactions on Biomedical Engineering. vol. 39(9), pp. 928-934, Sep. 1992.

International Search Report and Written Opinion for Application No. PCT/US2011/065463, mailed Aug. 22, 2012. (11 pages).

Masuzawa, T., et al., Set-up, Improvement, and Evaluation of an Electrohydraulic Total Artificial Heart with a Separately Placed Energy Converter. (1996) ASAIO Journal, vol. 42; M328-M332.

Matsuki et al. Energy Transferring System Reducing Temperature Rise for Implantable Power Consuming Devices. Proceedings of the 18th Annual Conference of the IEEE Engineering in Medicine and Biology Society, Amsterdam Oct. 31-Nov. 3, 1996, vol. 1, pp. 185-186.

Matsuki et al., Signal Transmission for Implantable Medical Devices using Figure-of-eight Coils, IEEE Transactions on Magnetics, vol. 32 No. 5, pp. 5121-5123, Sep. 1996.

Melvin, D.B., et al., Electric Power Induction Through an Isolated Intestinal Pouch. (1991) Trans. Am. Soc. Intern. Organs, vol. XXXVII;M203-M204.

Miller et al. Development of an Autotuned Transcutaneous Energy Transfer System. ASAIO Journal. 1993;39:M706-M710.

Mitamura et al. Development of an Implantable Motor-Driven Assist Pump System. IEEE Transactions on Biomedical Engineering. vol. 37(2), pp. 146-156, 1990.

Mitamura et al. A Transcutaneous Optical Information Transmission System for Implantable Motor-drive Artificial Hearts. ASAIO Transactions.1990;36:M278-M280.

Mohammed et al. A miniature DC-DC converter for energy producing implantable devices. IEEE Ninth Annual Conference of the Engineering in Medicine and Biology Society, 1147-1148, 1987.

Mohammed, Design of radio frequency powered coils for implantable stimulators. IEEE Ninth Annual Conference of the Engineering in Medicine and Biology Society, 1378-1379, 1987.

Mussivand et al. Remote energy transmission for powering artificial hearts and assist devices. Artificial Heart 6/6th International Symposium on Artificial Heart and Assist Devices. Akutsu et al., eds., Springer-Verlag, Tokyo, pp. 344-347, 1998.

Mussivand et al. Transcutaneous energy transfer system performance evaluation. Artificial Organs. May 1993;17(11):940-947.

Myers et al. A transcutaneous power transformer. Transactions of the American Society for Artificial Internal Organs, vol. 14, pp. 210-214, 1968.

Phillips, R.P., A High Capacity Transcutaneous Energy Transmission System. ASAIO Journal, vol. 41: M259-M262 (1995).

Rintoul et al, Continuing Development of the Cleveland Clinic-Nimbus Total Artificial Heart. ASAIO Journal, 39: M168-171 (1993).

(56) References Cited

OTHER PUBLICATIONS

Rosenberg et al., Progress Towards a Totally Implantable Artificial Heart. Cardiovascular Science & Technology: Basic & Applied, I. Precised Proceedings, pp. 214-216 (1989-1990).

Sherman et al., Energy Transmission Across Intact Skin for Powering Artificial Internal Organs. Trans. Am. Soc. Artificial Intern Organs, vol. XXVII, 1981, pp. 137-141.

Sherman et al., Transcutaneous energy transmission (TET) system for energy intensive prosthetic devices. Progress in Artificial Organs. 1985;400-404.

Sutton, A miniaturized device for electrical energy transmission through intact skin-concepts and sesults of initial tests. Third Meeting of the International Society for Artificial Organs. vol. 5, abstracts, Jul. 1981, pp. 437-440.

Weiss et al. A telemetry system for the implanted total artificial heart and ventricular assist device. IEEE Ninth Annual Conference of the Engineering in medicine and Biology Society, pp. 186-187, 1987.

Weiss et al., Permanent Circulatory Support at the Pennsylvania State University. IEEE Transaction on Biomedical Engineering 37(2):138-145 (Feb. 1990).

\* cited by examiner

METHOD AND APPARATUS FOR ACCURATELY TRACKING AVAILABLE CHARGE IN A TRANSCUTANEOUS ENERGY TRANSFER SYSTEM

RELATED APPLICATIONS

This application claims priority to U.S. Provisional Application Ser. No. 61/425,162, filed on Dec. 20, 2010, and entitled "Method and Apparatus for Accurately Tracking Available Charge in a Transcutaneous Energy Transfer System."

FIELD

The invention relates to transcutaneous energy transfer (TET) systems and more particularly to an improved device and method for accurately tracking battery charge in a TET system and providing a patient with an accurate battery runtime.

BACKGROUND

Many medical devices adapted for implantation also have high power requirements and must be frequently connected to external power sources. Inductively coupled transcutaneous energy transfer (TET) systems are increasingly popular for use in connection with these high-power implantable devices. A TET system may be employed to supplement, replace, or charge an implanted power source, such as a rechargeable battery. Unlike other types of power transfer systems, TET systems have an advantage of being able to provide power to the implanted electrical and/or mechanical device, or recharge the internal power source, without puncturing the skin. Thus, possibilities of infection are reduced and comfort and convenience are increased.

TET devices include an external primary coil and an implanted secondary coil, separated by intervening layers of tissue. The primary coil is designed to induce alternating current in the subcutaneous secondary coil, typically for transformation to direct current to power an implanted device. TET devices therefore also typically include an oscillator and other electrical circuits for providing appropriate alternating current to the primary coil. These circuits typically receive their power from an external power source.

TET systems commonly include an implanted rechargeable battery pack that can be used to power any implanted devices when the external power source is not available. However, when disconnected from the external power source patients are often unsure of how long the internal battery pack will last before requiring a charge cycle. Prior art methods of calculating remaining charge are based on the battery voltage, not the actual remaining charge. Because the battery voltage is not linear with respect to charge, these methods can report a near total charge for a long period of time and then quickly approach total exhaustion rather than report a linear decrease over time. This misleading indication of battery charge can be extremely risky for patients that depend on their implanted TET system for survival and who may not be able to immediately reconnect to an external power or charge source.

SUMMARY

To overcome the above and other drawbacks of conventional systems, the present invention provides improved methods and devices for tracking the charge and discharge of a battery pack, or charge storage device, in a transcutaneous energy transfer (TET) system.

One aspect of the invention provides a method of tracking power consumption and replenishment in a transcutaneous energy transfer system including determining the current charge remaining in a battery pack and measuring the current rate of power consumption for a cardiac assist device, determining the remaining time before the energy level of the battery pack is below a predetermined threshold level at the measured rate of power consumption, and communicating the remaining time before exhaustion of the battery pack to a user.

In one embodiment, these steps are repeated in an iterative manner to update the remaining time reported to the user.

In certain embodiments, the remaining time can be communicated to a user via an external display, while in other embodiments a vibratory or auditory signal is used to communicate the remaining time before exhaustion of the battery pack.

A second aspect of the invention provides an implantable device including a cardiac assist device, a rechargeable battery pack, and a controller. The controller is connected to the cardiac assist device and the rechargeable battery pack. The controller is configured to measure the charge level of the battery pack and power consumption rate of the cardiac assist device. The controller is further configured to compute the remaining time before the battery pack charge level reaches a predetermined threshold level and communicate that time to a user.

In one embodiment, the controller is further configured to repeatedly measure the battery charge level and power consumption rate and continually communicate the updated remaining time to the user. The controller can predict remaining battery time based on historic load monitoring and remaining battery capacity.

In certain embodiments, the controller communicates the remaining time to the user via an external display. In other embodiments, the controller can use a vibratory or auditory signal to communicate the remaining time to the user.

BRIEF DESCRIPTION OF THE DRAWINGS

The invention will be more fully understood from the following detailed description taken in conjunction with the accompanying drawings, in which.

DETAILED DESCRIPTION

Figure 1:
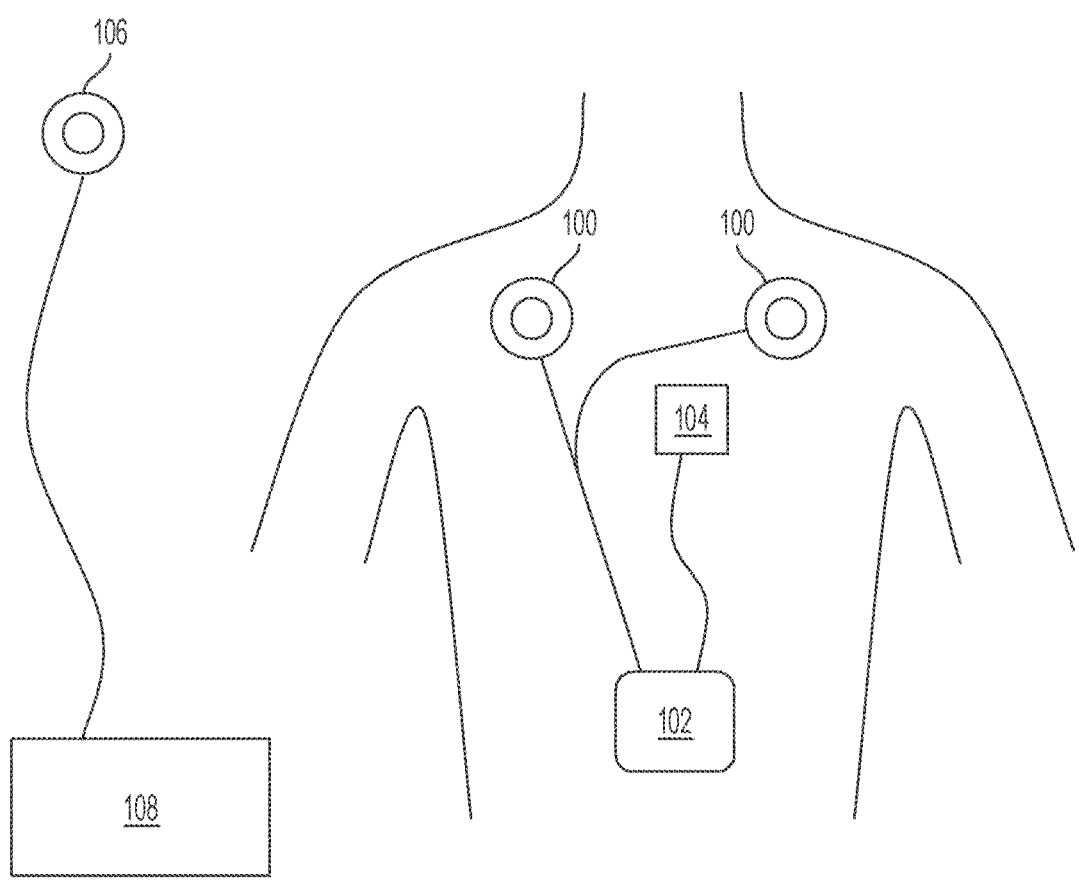
FIG. 1 is a diagram of an exemplary TET system with the implantable device of the present invention.

Certain exemplary embodiments will now be described to provide an overall understanding of the principles of the methods and devices disclosed herein. One or more examples of these embodiments are illustrated in the accompanying drawings. Those skilled in the art will understand that the methods and devices specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

A transcutaneous energy transfer (TET) system works by inductively coupling a primary coil to a secondary coil. The primary coil, configured for disposition outside a patient, is connected to a power source and creates a time-varying magnetic field. When properly aligned with a secondary coil, the time-varying magnetic field from the primary coil induces an alternating electric current in the secondary coil. The secondary coil is configured for implantation inside a patient and can be connected to a controller that harnesses the electric current and uses it to, for example, charge a battery pack or power an implantable device like a ventricular assist device (VAD), cardiac assist device, or other implantable device. By utilizing induction to transfer energy, TET systems avoid having to maintain an open passage through a patient's skin to power an implantable device.

TET systems include an implanted rechargeable battery pack that allows a patient to spend some amount of time disconnected from the external primary coil and power source. A controller connected to the rechargeable battery pack is configured to measure its charge and alert the patient, based on remaining runtime, when the battery is nearly exhausted.

Prior art methods and devices determine the remaining charge based on the voltage of the battery pack itself. This can be misleading, however, because the relationship between battery voltage and remaining charge is not linear. As a result, the battery may report a full charge for a longer than expected period of time. Worse still, after the measured voltage of the battery begins to drop, it may rapidly fall to a state of full exhaustion. This is extremely risky for patients with implanted TET systems because, in many cases, their consciousness and survival depends on the operation of the battery pack and connected cardiac assist device.

The present invention solves these problems by providing an implantable device and method of tracking power consumption in a TET system that measures the remaining charge in a battery pack as well as the power consumption rate of an attached cardiac assist device, calculates the remaining time before the charge level of the battery pack reaches a predetermined threshold level at the measured consumption rate, and communicates the time remaining to a user. This method provides users with a more accurate indication of the time remaining before a charge cycle will be required. This, in turn, improves patient quality of life by providing a more confident estimate of the time period during which the external power supply is not required.

FIG. 1 shows a diagram of an exemplary TET system of the present invention. An implantable device comprises a plurality of secondary coils 100, or a single secondary coil, adapted for disposition in a patient. The secondary coil(s) are connected to a controller 102 that is adapted to receive electric current from a single or a plurality of secondary coils for use or storage. The controller can then direct the electric current to, for example, charge a battery (which can be integrated with controller 102) or power a ventricular assist device 104 or other implantable device.

FIG. 1 also shows an exemplary embodiment of primary coil 106 that is adapted to remain outside the body and transfer energy inductively to the secondary coil(s). Primary coil 106 is connected to an external power source, which can include, for example, conditioning and control circuitry. Optionally, more than one primary coil 106 can be used simultaneously with the multiple secondary coils 100 to reduce the time required to charge an implanted battery.

In use, primary coil(s) 106 are placed over the area of secondary coils 100 such that they are substantially in axial alignment. Power source 108, which can include conditioning circuitry to produce a desired output voltage and current profile, is then activated to produce a time-varying magnetic field in the primary coil(s) 106. The time-varying magnetic field induces an electric current to flow in the secondary coils 100 and the current is subsequently distributed to controller 102 and any attached ventricular assist devices 104 or charge storage devices.

Figure 2:
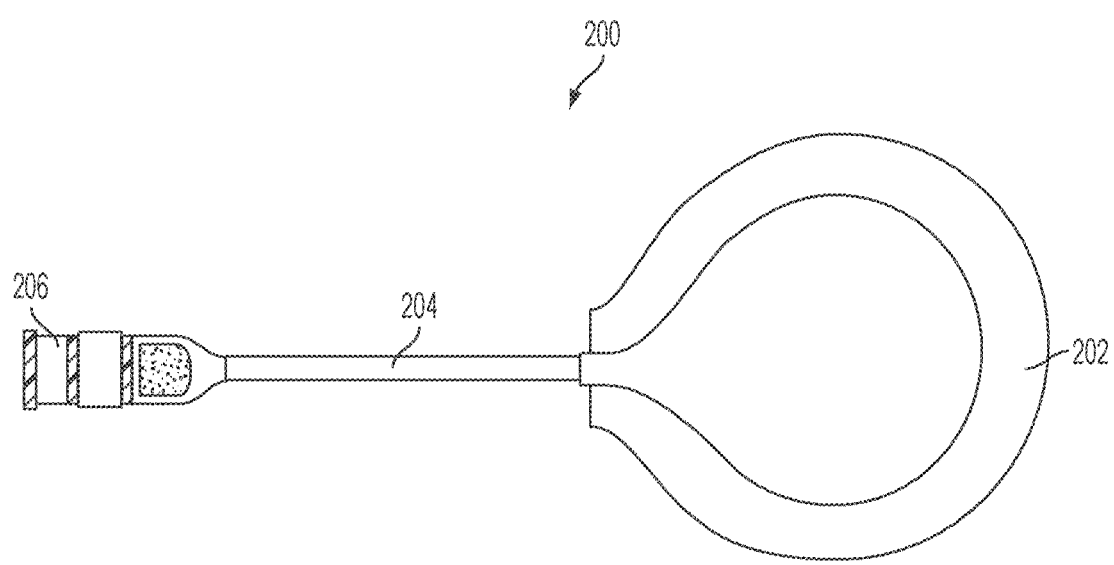
FIG. 2 is an illustration of an exemplary implantable secondary coil.

FIG. 2 illustrates an exemplary secondary coil 200 adapted for disposition in a patient. Secondary coil 200 features a coil portion 202 consisting of several turns of conductive wire, a connecting portion 204, and an optional interface portion 206. Coil portion 202 can vary in size and turns of wire depending on numerous factors such as the intended implantation site. In an exemplary embodiment, coil portion 202 comprises 12 turns of Litz wire in a two-inch diameter coil. In addition to the wire, the coil 202 can contain a ferrous core and electronic circuitry which rectifies the AC current and communicates with the external coil and driver to provide a regulated DC output voltage. An exemplary secondary coil is described in U.S. Patent Pub. No. 2003/0171792, which is incorporated herein by reference.

The coil portion 202 is electrically coupled to the connecting portion 204, which can be formed from a segment of the same wire used to form the coil portion. The length of connecting portion 204 can also vary based on, for example, the distance from the implantation site of a secondary coil to that of a controller.

Connecting portion 204 is also electrically coupled to optional interface portion 206. Interface portion 206 is used to connect the secondary coil 200 to a controller 102. The interface portion can include any electrical connector known in the art to facilitate modular connection to a controller 102, or can consist of a terminal end of the connecting portion 204 that is capable of being electrically connected to a controller.

Figure 3:
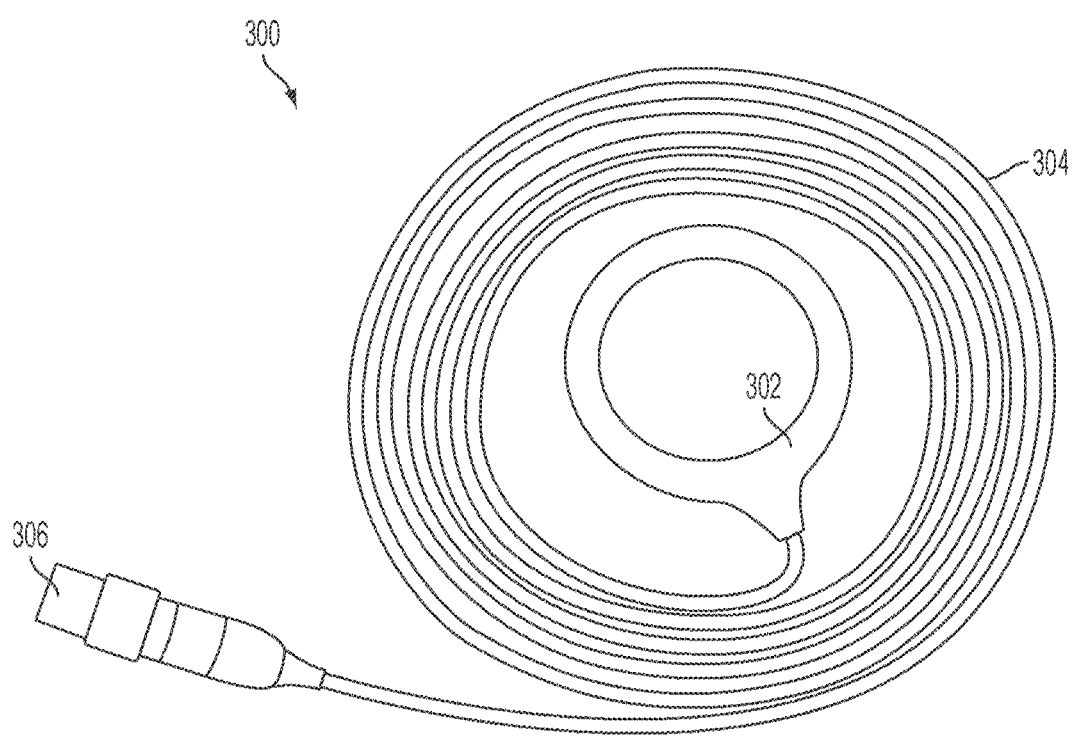
FIG. 3 is an illustration of an exemplary primary coil.

FIG. 3 shows an exemplary primary coil 300 configured to transmit transcutaneous energy to a secondary coil like that illustrated in FIG. 2. Similar to secondary coil 200 in FIG. 2, primary coil 300 can include a coil portion 302, a connecting portion 304, and an interface portion 306. Primary coil 300 is adapted for disposition outside the patient, however, and induces electric current in secondary coil 200 by emitting a time-varying magnetic field from coil portion 302.

Coil portion 302 can vary in size and turns of wire depending on several factors including, for example, the size of any secondary coils it will be used with. Coil portion 302 is electrically coupled to connecting portion 304. Connecting portion 304 can be formed from a portion of the wire used to form coil portion 302. Connecting portion 304 can vary in length depending on any of several factors including, for example, how far a patient is from a power source. Connecting portion 304 is in turn electrically coupled to interface portion 306, which is adapted to connect to a power source (or associated conditioning or control circuitry) like power source 108 of FIG. 1. Interface portion 306 can include any electrical connector known in the art to facilitate modular connections to external power source 108, or can consist of a terminal end of connecting portion 304 that is adapted to be electrically connected to power source 108.

Figure 4:
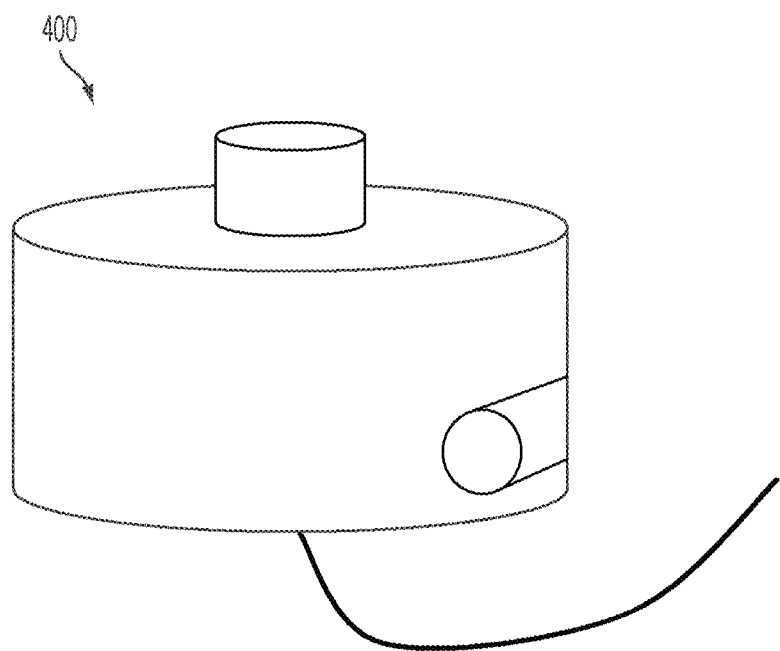
FIG. 4 is a front perspective view of an exemplary ventricular assist device powered by a TET system.

Primary coil 300 is used to transfer power transcutaneously in order to ultimately support an implantable device like the ventricular assist device (VAD) 400 depicted in FIG. 4. The ventricular assist device 400 aids the heart in circulating blood through the body. While a ventricular assist device is an exemplary embodiment of an implantable device that can benefit from TET systems, it is by no means the only implantable device that can be powered in this way. Other cardiac assist devices, as well as many other types of powered implantable devices, can be used with the system of the present invention.

Figure 5:
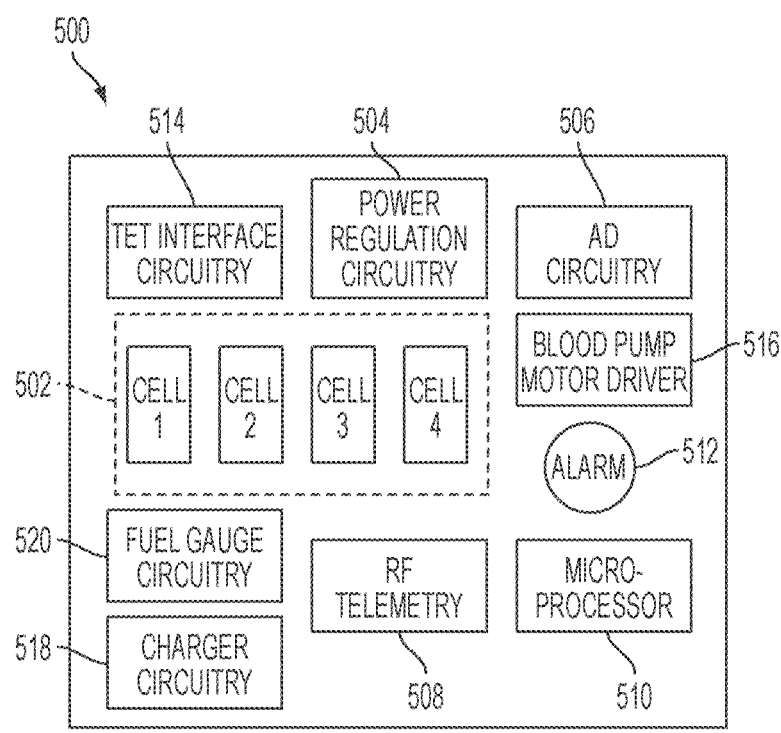
FIG. 5 is a diagram of an exemplary implantable controller containing power and control circuitry, as well as a rechargeable battery pack.

FIG. 1 shows the secondary coils 100 connected to the ventricular assist device 104 via a controller like that illustrated in FIG. 5. FIG. 5 depicts an integrated controller and battery pack 500 that is adapted for disposition in a patient. The rechargeable battery pack includes battery cells 502 that can be charged using the electric current received from the secondary coil(s) 100. Electric current received from the secondary coil(s) 100 is processed through the TET interface circuitry 514 and conditioned for use with the battery cells 502 through the charger circuitry 518 or to power the internal electronics and ventricular assist device 104 by power regulation circuitry 504. Power regulation circuitry 504 can contain any of several circuit designs known in the art that are effective to convert the voltage and current received from the TET interface circuitry 514 into a desired output voltage and current that can be used to power the internal electronic circuitry 506, 508, 510, 512 and the ventricular assist device 104 via the blood pump motor driver 516.

Controller 500 can also include VAD circuitry 506 and 516 that is configured to control the ventricular assist device 104. The VAD circuitry can include monitoring features so that any failures in the ventricular assist device 104 are detected in the controller 500. The controller 500 can further include a central processor 510 that coordinates functions executed by the charger circuitry 518, power regulation circuitry 504, blood pump motor driver circuitry 516, and A/D circuitry 506.

The processor 510 also monitors the function of secondary coils 100 and ventricular assist device 104. If a fault is detected in either component, processor 510 can utilize RF telemetry module 508 to allow it to communicate fault information with a user via an external display or control console. The display or control console could take the form of a common desktop computer, mobile phone, PDA, bed-side control console, or any other type of computing or signaling device known in the art. The fault information communicated to a user can also be in the form of an alarm sounded by a display or control console as described above. Alternatively, controller 500 can include an alarm module 512 that can sound a vibratory alarm in the event of a failure. In addition, the external power source 108 can also be configured to detect a fault in a coupled secondary coil 100 and alert a patient accordingly.

Controller 500 also includes fuel gauge circuitry 520 that is configured to measure both the current charge remaining in battery cells 502 and the power consumption rate of the VAD 104. To determine remaining charge, the fuel gauge circuitry 520 records a plurality of metrics such as battery impedance, open-circuit voltage, temperature, discharge rate, and cell aging. The resulting measurement is more accurate than prior art systems that gauge charge based on voltage alone.

Monitoring these additional battery cell metrics has other benefits as well. For example, charging rate can be adjusted based on battery cell temperature to prevent prolonged periods of time at high temperatures. Reducing the operating temperature of the battery in this way slows cell aging and reduces the need to exchange the battery pack. In addition, fully monitored discharge/charge cycles can be conducted while safely connected to an external power source. Periodically conducting these full discharge/charge cycles improves cycle life when the patient is away from the external power source.

An exemplary system for accurately determining battery charge is the bq20z95 platform by Texas Instruments, Inc. featuring the Impedance Track™ gauging technology. More information on this system can be found at focus.ti.com/lit/an/slua364/slua364.pdf and focus.ti.com/lit/ds/slus757b/slus757b.pdf. These publications are hereby incorporated by reference in their entirety. One of skill in the art will appreciate that other power tracking systems that provide similar or better accuracy can be used and the bq20z95 platform is offered by way of example only.

After determining an accurate level of charge remaining in the battery cells 502 and the power consumption rate of the VAD 104, fuel gauge circuitry 520 or microprocessor 510 can compute the remaining time, based on the current level of consumption, until the battery reaches a predetermined threshold level. This can be done, for example, by dividing a measured amount of charge (which can be expressed as a unit of electrical charge) by a measured consumption rate (which can be expressed as a unit of electrical charge per unit of time). The result is the expected time until the measured amount of charge is depleted. This calculation can be adjusted to measure expected time until a predetermined threshold level of charge is reached by simply subtracting the threshold level of charge from the measured level of charge before calculation. One of skill in the art may appreciate alternative methods for calculating the remaining time until the battery reaches a predetermined level, all of which are considered within the scope of the invention.

The predetermined threshold level can be set above the level of battery exhaustion to provide some reserve time and allow a patient to get to an external power source. In addition, multiple threshold levels may be set to provide a patient with multiple warnings as the battery exhausts itself.

Figure 6:
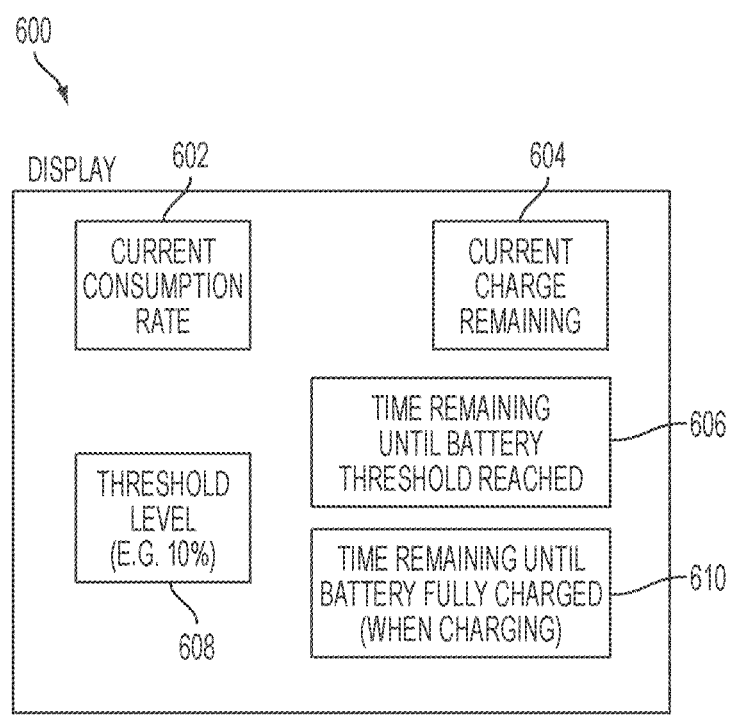
FIG. 6 is an illustration of an exemplary display for communicating remaining charge time to a user.

The microprocessor 510 can use RF telemetry module 508 or alarm module 512 to communicate the remaining time to a user. For example, and as illustrated in FIG. 6, the RF telemetry module 508 can be used to communicate the remaining time to a user via an external display 600. External display 600 may be any display known in the art, including displays integrated in control consoles or diagnostic equipment, PDAs, laptop or desktop computers, etc.

When operating on battery power the external display 600 can be configured to display the current consumption rate 602 and current charge remaining 604 as measured by the fuel gauge & charger circuitry 518, the threshold level 608 in use, and the time remaining 606 until the battery reaches that threshold level. When the primary coil 106 is coupled with the secondary coil 100, the external display 600 can be configured to display the time until the battery is fully charged 610. One of skill in the art will appreciate that many different combinations of this and other operating data can be communicated from the controller 500 to the external display 600 using the RF telemetry module 508.

In other embodiments, the controller 500 may communicate the time remaining by a vibratory signal to the patient. In these embodiments, alarm module 512 is configured to create the vibratory signal, or RF telemetry module 508 can be used to communicate with an auditory or vibratory signaling device located outside the controller 500.

In the case of auditory signaling, the signal may be in the form of an announcement of the time remaining, or may be a series of beeps that signifies the remaining charge level. In the case of vibratory signaling, the signal may be a series of on-off or timed vibrations that signal the remaining charge level. For example, if the threshold level was set to 30 minutes, when the charge capacity of the battery cells 502 reaches 30 minutes the alarm module 512 may create a vibratory signal for 3 seconds every 30 seconds until the external power source is applied. Similarly, a critically low threshold level may be set to 15 minutes and, when the capacity of the battery cells 502 reaches that level, the alarm module 512 may create a vibratory signal for 3 seconds every 10 seconds until the external TET is applied. The alarm thresholds and vibrator patterns are configurable in software depending on patient, healthcare professional, or manufacturer requirements. As a last resort, the VAD can be configured to automatically enter a low-power mode in order to extend the runtime of the device.

The method of the present invention may be executed once to determine the remaining time until the battery cells 502 reach a given threshold level, or the method steps may be repeatedly iterated to provide a continually updating estimate of the time remaining, which may change due to variations in the power consumed by the VAD. One of skill in the art will appreciate that a hybrid of these two methods is possible as well—the method steps may be iterated on a schedule, e.g. once every two minutes, and a timer can be used in the interim to count down from the last computed remaining time estimate.

Figure 7:
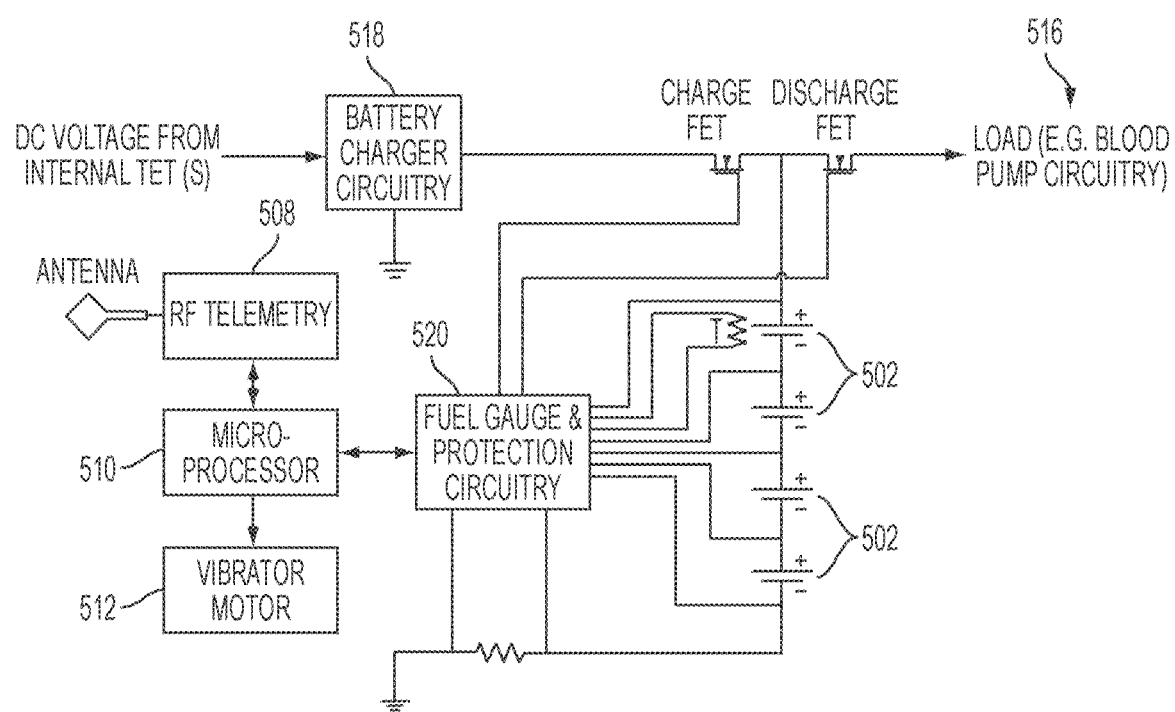
FIG. 7 is an exemplary circuit diagram of the controller illustrated in FIG. 1.

FIG. 7 illustrates an exemplary circuit diagram for the implantable device of the present invention. The diagram illustrates the electrical connections between the VAD circuitry (including blood pump motor driver 516), battery cells 502, fuel gauge circuitry 520, battery charger circuitry 518, microprocessor 510, RF telemetry module 508, and alarm module 512. One of skill in the art will appreciate that this is an exemplary circuit diagram only, and there are several other configurations that would also be effective to create the implantable device of the present invention.

The system of the present invention provides several benefits over prior art TET systems. For example, the method of the present invention provides a more accurate estimate of the time remaining until the rechargeable battery pack reaches a predetermined threshold level. This allows patients to more confidently plan their time away from an external power source and improves their quality of life.

All papers and publications cited herein are hereby incorporated by reference in their entirety. One skilled in the art will appreciate further features and advantages of the invention based on the above-described embodiments. Accordingly, the invention is not to be limited by what has been particularly shown and described, except as indicated by the appended claims.

What is claimed is:

1. A method of accurately tracking available charge stored in a transcutaneous energy transfer system, comprising:
utilizing fuel gauge circuitry to record a plurality of metrics of a transcutaneous energy transfer system associated with an implantable device, said plurality of metrics including battery temperature;
utilizing a controller to determine the current charge remaining in a rechargeable battery pack based on said plurality of metrics;
utilizing the fuel gauge circuitry to measure the current rate of power consumption for the implantable device;
utilizing the controller to determine the remaining time before the energy level of the battery pack is below a predetermined threshold level at the measured rate of power consumption; and
utilizing the controller to communicate the remaining time before exhaustion of the battery pack to a user.

2. The method of claim 1, wherein the steps are repeated in an iterative manner to update the remaining time before exhaustion of the battery pack.

3. The method of claim 1, wherein the remaining time is communicated to the user via an external display.

4. The method of claim 1, wherein the remaining time is communicated to the user via an internal vibratory signal.

5. The method of claim 1, wherein the remaining time is communicated to the user via an external auditory signal.

6. An implantable device, comprising:
an implantable assist device;
a rechargeable battery pack; and
a controller connected to the implantable assist device and rechargeable battery pack;
wherein the controller is configured to measure the charge level of the battery pack, based on a plurality of metrics, said metrics including battery temperature, measure a power consumption rate of the implantable assist device, compute the remaining time before the battery pack energy level reaches a predetermined threshold level, and communicate the remaining time to a user.

7. The device of claim 6, wherein the controller repeatedly measures the available charge level and power consumption rate and continually communicates the updated remaining time to the user.

8. The device of claim 6, wherein the controller communicates the remaining time to the user via an external display.

9. The device of claim 6, wherein the controller communicates the remaining time to the user via a vibratory signal.

10. The device of claim 6, wherein the controller communicates the remaining time to the user via an auditory signal.

11. The device of claim 6, wherein the implantable assist device is a ventricular assist device.

12. The device of claim 6, wherein the controller is further configured to control a charging rate of the rechargeable battery pack based in part on the battery temperature.

13. The method of claim 1, comprising recharging the rechargeable battery pack at a battery charging rate and controlling the battery charging rate based in part on the battery temperature.

* * * * *